United States Patent
Real et al.

(10) Patent No.: US 10,433,871 B2
(45) Date of Patent: Oct. 8, 2019

(54) INTRAOSSEOUS DEVICE

(71) Applicant: PROMETHEUS MEDICAL TECHNOLOGIES LIMITED, Herefordshire (GB)

(72) Inventors: Keith Joseph Real, Herefordshire (GB); Malcolm Quentin Russell, Herefordshire (GB)

(73) Assignee: PROMETHEUS MEDICAL TECHNOLOGIES LIMITED, Herefordshire (GB)

( * ) Notice: Subject to any disclaimer, the term of this patent is extended or adjusted under 35 U.S.C. 154(b) by 238 days.

(21) Appl. No.: 15/497,770

(22) Filed: Apr. 26, 2017

(65) Prior Publication Data
US 2017/0311981 A1 Nov. 2, 2017

(30) Foreign Application Priority Data

Apr. 28, 2016 (EP) .................... 16167438
Feb. 23, 2017 (EP) .................... 17157674
Mar. 14, 2017 (EP) .................... 17160940

(51) Int. Cl.
A61B 17/34 (2006.01)
A61B 17/16 (2006.01)

(52) U.S. Cl.
CPC ........ *A61B 17/3472* (2013.01); *A61B 17/164* (2013.01); *A61B 17/3415* (2013.01); *A61B 17/3421* (2013.01)

(58) Field of Classification Search
CPC . A61B 17/34; A61B 17/3415; A61B 17/3417; A61B 17/3421; A61B 17/3423;
(Continued)

(56) References Cited

U.S. PATENT DOCUMENTS 4,487,209 A 12/1984 Mehl
4,838,282 A 6/1989 Strasser et al.
(Continued)

FOREIGN PATENT DOCUMENTS

EP      1 925 261 A1   5/2008
WO  2005/072625 A2   8/2005
(Continued)

OTHER PUBLICATIONS

Search Report issued in corresponding GB Application No. GB1706611.9 dated Sep. 28, 2017; 2pp.
(Continued)

Primary Examiner — Melanie R Tyson
(74) Attorney, Agent, or Firm — Studebaker & Brackett PC

(57) ABSTRACT

An intraosseous device includes a stylet with a pointed end for penetrating bone and a cannula through which the stylet extends. The stylet has a bent portion which is engaged in a receiver in a handle cover. The cannula has an outwardly extending flare which is engaged in a corresponding seat in a hub. The handle and the hub have formations which interlock with one another when the tip of the stylet is aligned with the tip of the cannula. The interlock formations further assist torque transmission. The configuration ensures that the maximum manual torque can be applied to penetrate bone while ensuring that the stylet and cannula are aligned for maximum cutting efficiency and remain fixed to the handle and the hub respectively.

24 Claims, 15 Drawing Sheets

(58) Field of Classification Search
CPC ............ A61B 17/3472; A61B 17/3476; A61B 2017/3445; A61B 2017/348
See application file for complete search history.

(56) References Cited

U.S. PATENT DOCUMENTS

| | | | |
|---|---|---|---|
| 5,257,632 A * | 11/1993 | Turkel | A61B 10/025 |
| | | | 600/567 |
| 5,372,583 A * | 12/1994 | Roberts | A61M 25/06 |
| | | | 600/567 |
| 6,217,561 B1 | 4/2001 | Gibbs | |
| 2002/0042581 A1 | 4/2002 | Cervi | |
| 2010/0298784 A1 | 11/2010 | Miller | |
| 2012/0010455 A1 | 1/2012 | Reichenbach et al. | |
| 2013/0041345 A1 | 2/2013 | Kilcoin et al. | |
| 2013/0096508 A1 * | 4/2013 | Beamer | A61B 17/3472 |
| | | | 604/180 |

FOREIGN PATENT DOCUMENTS

| | | |
|---|---|---|
| WO | 2008/054894 A2 | 5/2008 |
| WO | 2014/134438 A1 | 9/2014 |

OTHER PUBLICATIONS

International Search Report and Written Opinion issued in PCT/EP2017/059931 dated Jul. 5, 2017.

* cited by examiner

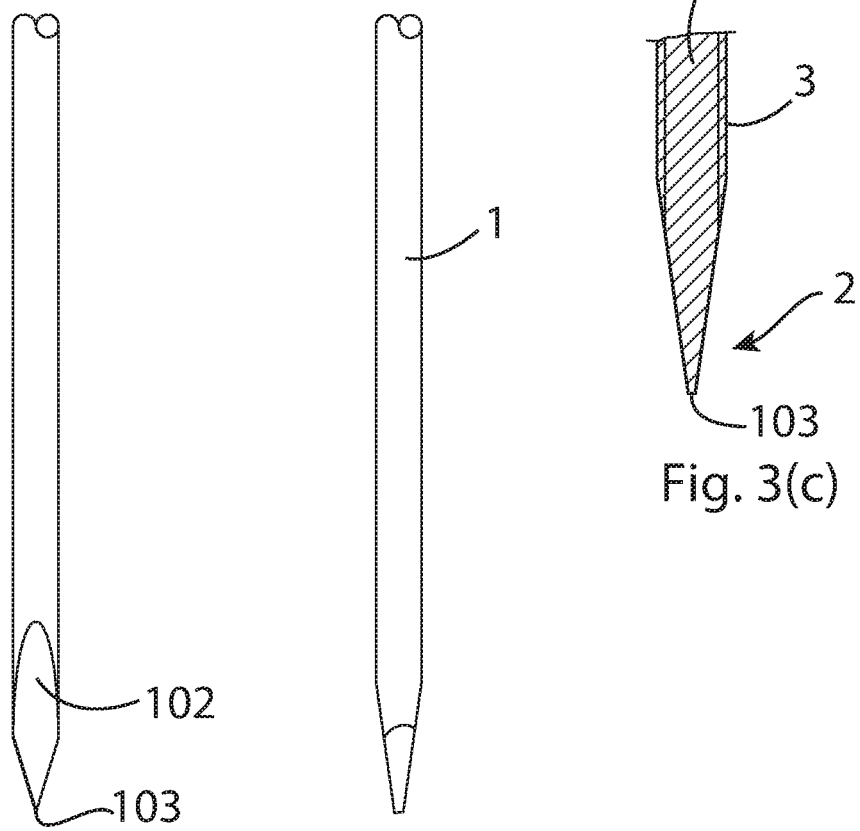
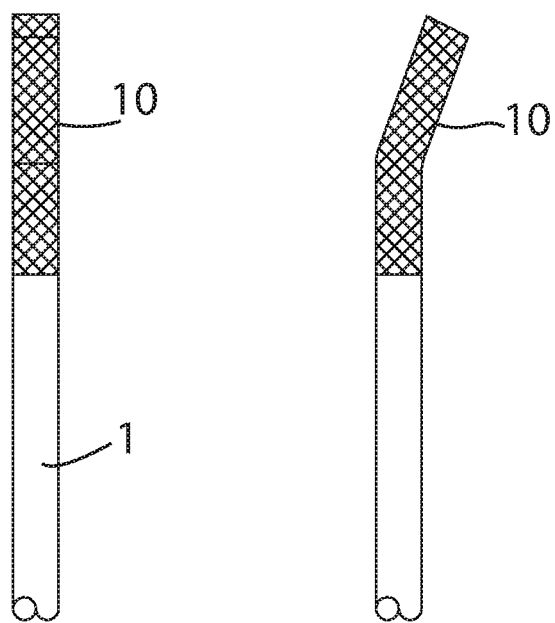
Fig. 3(a)　　Fig. 3(b)　　Fig. 3(c)

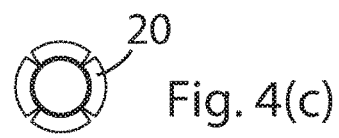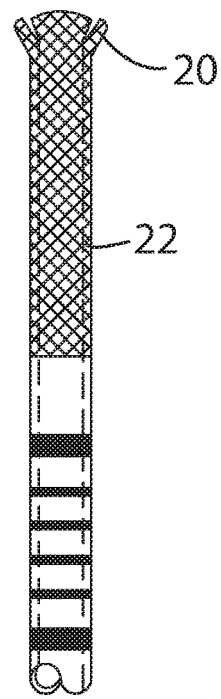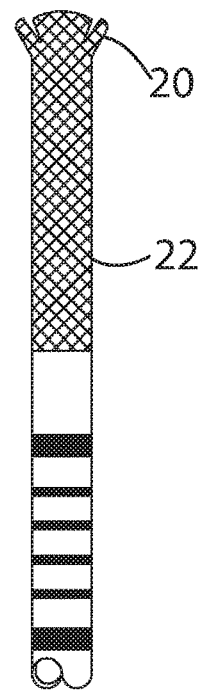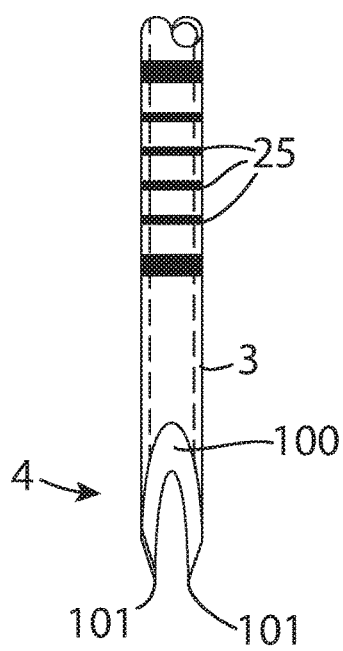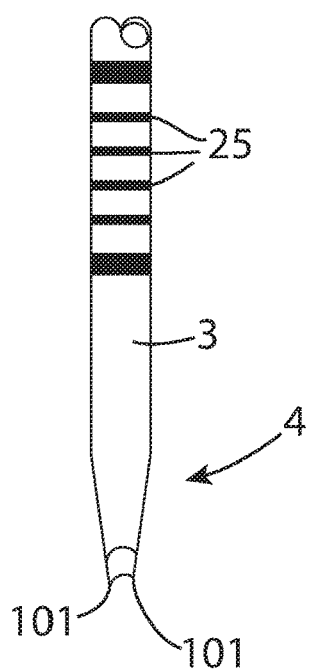
Fig. 4(a)   Fig. 4(b)

INTRAOSSEOUS DEVICE

INTRODUCTION

There are currently several different intraosseous devices commercially available and, in general, these are stainless steel needles with central removable stylets/trocars that reduce plugging risk during insertion. Studies and case reports on these products have shown that manual needles can be easily used in young paediatric patients. However, it has been seen that it is difficult to insert these in adults (S. M. Blumberg, 2008) (L. Phillips, 2010).

The failure mode of current intraosseous devices is primarily a failure to easily penetrate adult bone. There is therefore a need for an intraosseous device that can readily penetrate adult bone.

STATEMENTS OF INVENTION

According to the invention there is provided an intraosseous device comprising:—
   a handle;
   a hub which is releasably mounted to the handle;
   a stylet having an end mounted to the handle; and
   a cannula having an end mounted to the hub,
   wherein the handle end of the stylet has a bend and the handle has a receiver for the bent portion of the stylet for non-rotatably fixing the stylet to the handle;
   wherein the hub end of the cannula has an outwardly extending flare for non-rotatably fixing the cannula to the hub; and
   wherein the handle and the hub have interengagable formations for torque transmission.

In one embodiment the formations comprise a plurality of circumferentially spaced-apart handle formations that are engagable with a plurality of corresponding formations of the hub.

In one case the handle formations and the hub formations comprise interlock formations.

In one embodiment the handle is rotatable relative to the hub from a disengaged configuration in which the handle formations are not aligned with the hub formations to an aligned configuration in which the handle formations are aligned with the hub formations.

In the interlocked configuration, a tip of the stylet preferably extends from a distal end of the cannula. In the interlocked configuration, a bevelled edge of the stylet is preferably aligned with a bevelled edge of the cannula.

In one case in the aligned configuration, the handle is movable axially for interlocking the handle formations with the hub formations.

In one embodiment the plurality of hub formations comprise formations of differing shapes and the plurality of handle formations comprise formations of differing shapes and wherein, in the engaging configuration, handle formations of the same shape as formation of the hub are aligned. The handle formations and the hub formations may be engagable only in a set number of engagement configurations of the handle relative to the hub. In one case the set number is one.

In another case the set number is two and the engagement configuration are at 180° to each other.

In one embodiment the formations comprise ribs and corresponding recesses.

The formations may be of generally polygonal shape.

In one case the formations comprise at least one dovetail formation of the handle which in the engaged configuration is engaged with a corresponding dovetail formation of the hub.

The handle may comprise a pair of dovetail formations which are diametrically opposed. In one case the handle comprises two pairs of dovetail formations.

The invention also provides an intraosseous device comprising:—
   a handle;
   a hub which is releasably mounted to the handle;
   a stylet mounted to and extending from the handle;
   a cannula mounted to and extending from the hub;
   wherein the handle and the hub have interengagable formations for torque transmission to the stylet and the cannula for bone penetration on either clockwise or anticlockwise rotation of the device.

In one case the formations comprise a plurality of circumferentially spaced-apart handle formations that are engagable with a plurality of corresponding formations of the hub.

The handle formations and the hub formations may comprise interlock formations.

In some cases the handle is rotatable relative to the hub from a disengaged configuration in which the handle formations are not aligned with the hub formations to an aligned configuration in which the handle formations are aligned with the hub formations. In the interlocked configuration, a tip of the stylet may extend from a distal end of the cannula. In the interlocked configuration, a bevelled edge of the stylet may be aligned with a bevelled edge of the cannula.

In one case in the aligned configuration, the handle is movable axially for interlocking the handle formations with the hub formations.

In one embodiment the plurality of hub formations comprise formations of differing shapes and the plurality of handle formations comprise formations of differing shapes and wherein, in the engaging configuration, handle formations of the same shape as formation of the hub are aligned.

The handle formations and the hub formations may be engagable only in a set number of engagement configurations of the handle relative to the hub. The set number may be one. In one case the set number is two and the engagement configuration are at 180° to each other.

In some cases the formations comprise ribs and corresponding recesses. The formations may be of generally polygonal shape.

The formations may comprise at least one dovetail formation of the handle which in the engaged configuration is engaged with a corresponding dovetail formation of the hub. The handle may comprise a pair of dovetail formations which are diametrically opposed. The handle may comprise two pairs of dovetail formations.

According to the invention there is provided an intraosseous device comprising:—
   a handle;
   a hub which is releasably mounted to the handle;
   a stylet having an end mounted to the handle; and
   a cannula having an end mounted to the hub.

In some cases the handle is configured for manual operation and may comprise manual grip features. In other cases the handle is configured for connection to a powered driver.

The invention also provides an intraosseous device comprising:—
   a handle;
   a hub which is releasably mounted to the handle;

a stylet having an end mounted to the handle; and
a cannula having an end mounted to the hub,
wherein the handle is configured for connection to a powered driver for torque transmission.

In some embodiments the handle comprises drive formations for interengagement with corresponding formations of a powered driver.

In some cases the handle has a central formation for engaging with a corresponding central formation of a powered driver.

Also provided is a system comprising an intraosseous device of the invention and a powered driver which is adapted for releasable connection to the handle.

The powered driver may comprise a drive shaft, and the drive shaft has one end for connecting with the handle of the device. The powered driver may comprise a motor for providing rotary motion to the drive shaft. In one case the powered driver comprises a gear assembly rotatably attached to the motor. The powered driver may further comprise a power supply and electrical circuitry for providing power to the motor. The powered device may have at least one electronic switch. The switch may be an on/off switch which activates and de-activates the powered device. A switch may be used to increase or decrease the speed of rotation of the drive shaft. In some cases activation of a switch causes power to be supplied of either polarity so the motor can rotate in either a clockwise or anti-clockwise direction.

In one embodiment the handle end of the stylet has a bend and the handle has a receiver for the bent portion of the stylet for non-rotatably fixing the stylet to the handle.

Alternatively or additionally the hub end of the cannula has an outwardly extending flare for non-rotatably fixing the cannula to the hub.

In one case the bent portion of the stylet extends at an angle of from 10° to 30° to the longitudinal axis of the main body of the stylet. The bent portion of the stylet may extend at an angle of about 20° to the longitudinal axis of the stylet.

In one embodiment the bent portion of the stylet has a roughened surface.

In one case the flare at the hub end of the cannula is a split flare.

In one embodiment the hub end of the cannula has a roughened surface.

In one case the handle and the hub have interengagable formations for torque transmission.

The hub may comprise a circumferential flange part. The flange part may have cut-away regions to facilitate finger engagement with the hub.

In one embodiment the hub comprises a luer connector which is exposed on removal of the handle body.

The handle may comprise a handle body to which the handle end of the stylet is mounted and a handle cover which is mounted to the handle body. The handle body may comprise a socket to receive a corresponding spigot of the handle cover.

In one case the cover has a ledge extending around the periphery thereof and a depending wall and wherein the handle body has a corresponding recess to receive the depending wall of the handle cover.

In one embodiment both the handle body and the handle cover are generally rectilinear in transverse cross section with rounded corners. The handle body and the handle cover may have manual grip features.

In all embodiments the cannula may have a series of markings which may extend around the cannula. The markings are used to indicate to a user the length that the cannula has penetrated into bone. At distances such as every 5 mm along the length of the cannula the markings may be differentiated, for example made thicker, for ease of monitoring by the user.

In one embodiment the intraosseous device further comprises a removable protective tube for the stylet and cannula.

Also provided is an intraosseous system comprising an intraosseous device and a stabiliser for stabilising the device, in situ. Also provided is a stabiliser for use in stabilising an intraosseous device. The intraosseous device may be a device according to the various embodiments described herein.

In one embodiment the stabiliser comprises mounting features for engaging the stabiliser with the intraosseous device. The stabiliser may comprise side wings for mounting to the skin of a patient.

In one case the stabiliser comprises a pair of half cylindrical elements which are hinged together on one side and which have a locking system for interlocking the parts on an opposite side.

A side wing may extend outwardly from each of the half cylindrical elements.

In another embodiment the stabiliser comprises cushioning to engage with the hub at different locations and/or orientations of the hub.

BRIEF DESCRIPTION OF THE DRAWINGS

The invention will be more clearly understood from the following description thereof, given by way of example only, with reference to the accompanying drawings, in which:

FIGS. 3(a), (b) and (c) are a series of images showing a stylet part of the device;

FIGS. 4(a), (b) and (c) are views of a cannula part of the device;

DETAILED DESCRIPTION

Figure 1:
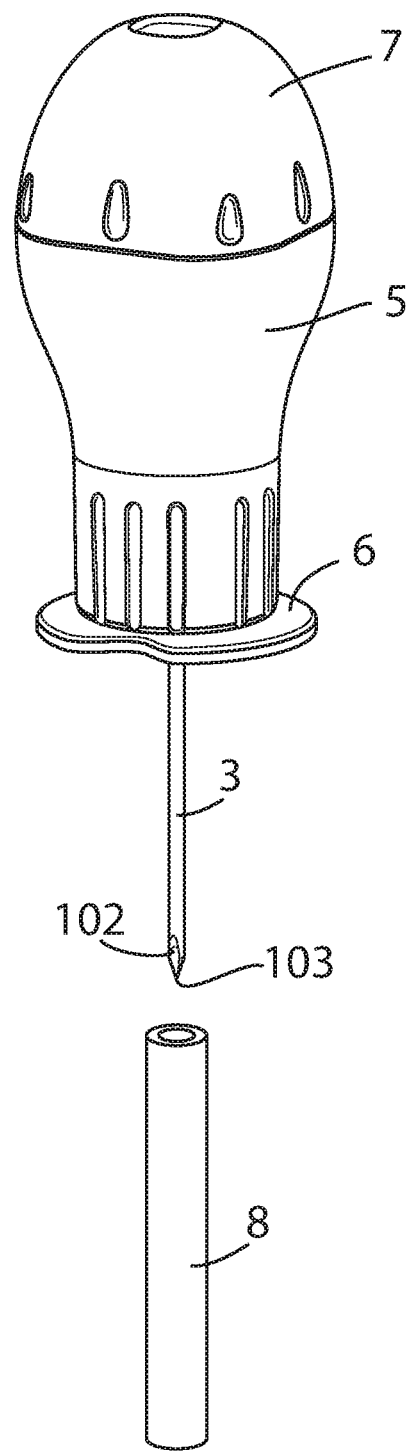
FIG. 1 is a perspective view of a manual intraosseous device according to the invention including a protective tube.
Figure 2:
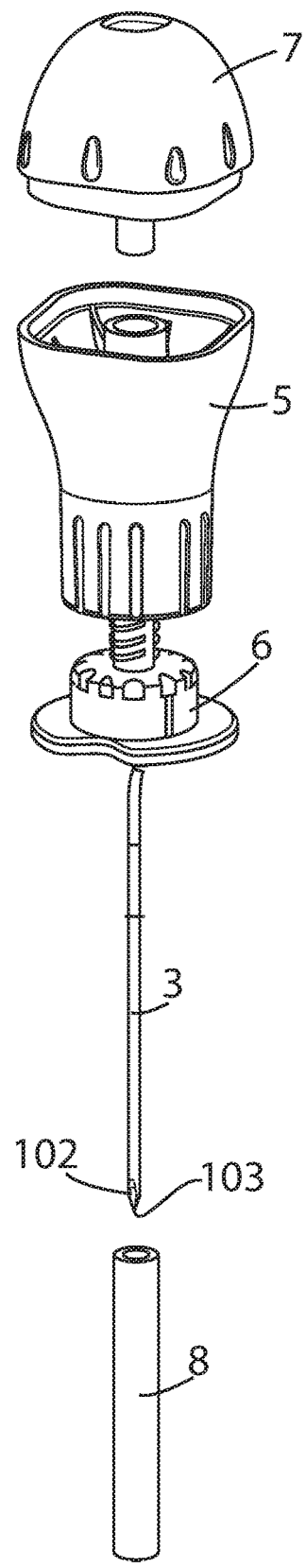
FIG. 2 is an exploded view of the device of FIG. 1.
Figure 5:
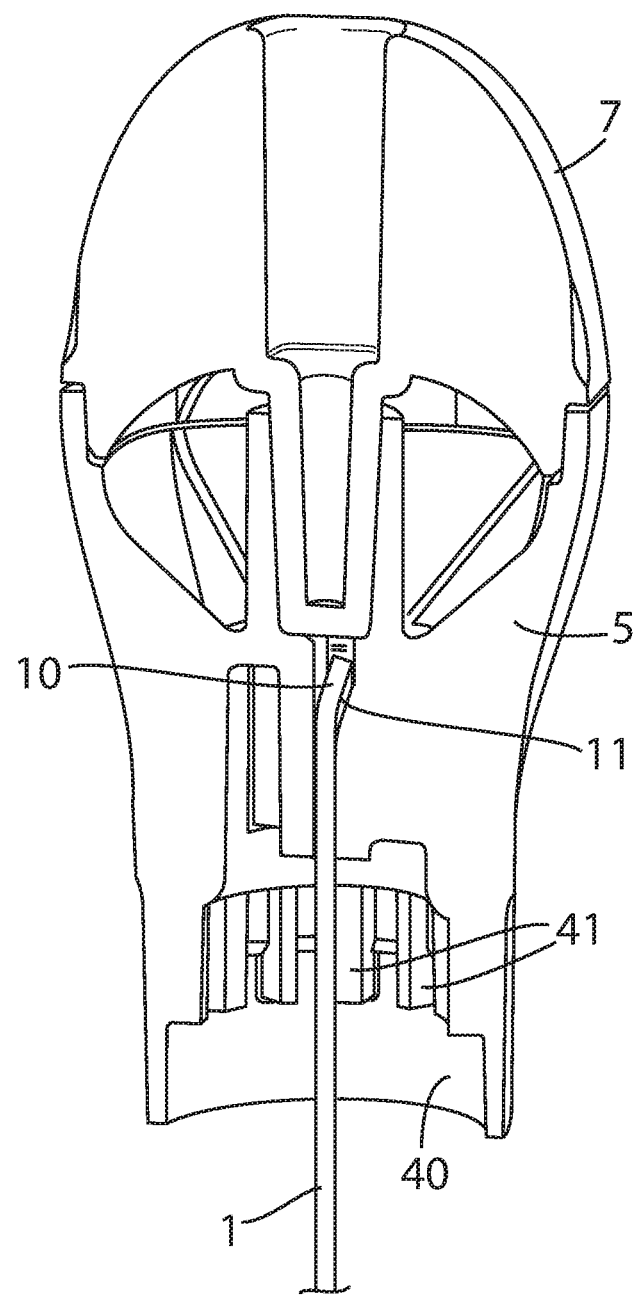
FIG. 5 is a cut-away view illustrating the mounting of the stylet in a handle body of the device.
Figure 6:
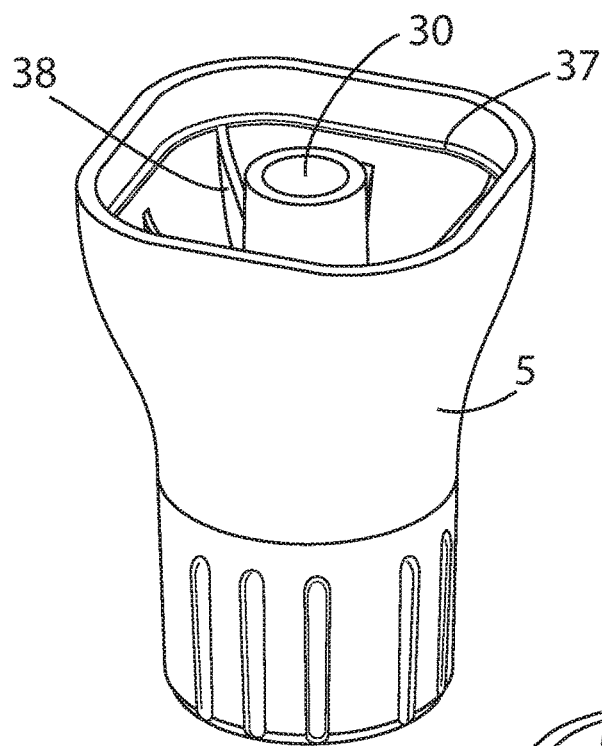
FIG. 6 is a perspective view of a handle body of the device.
Figure 7:
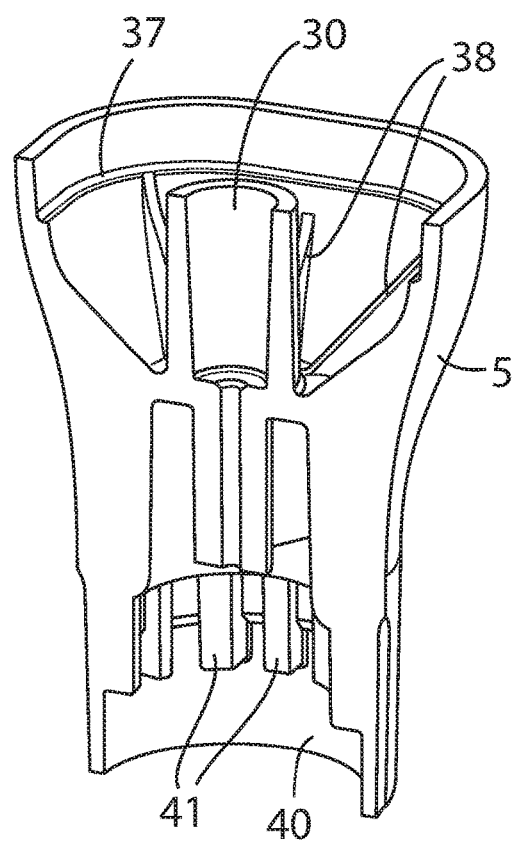
FIG. 7 is a cut-away view of the handle body.
Figure 8:
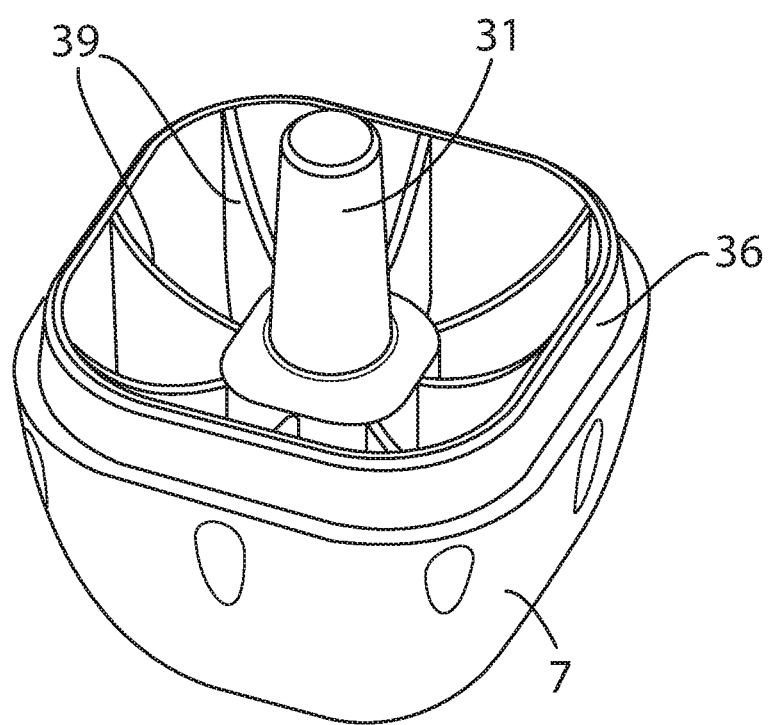
FIG. 8 is a perspective view of a head part forming a handle cover of the device.
Figure 9:
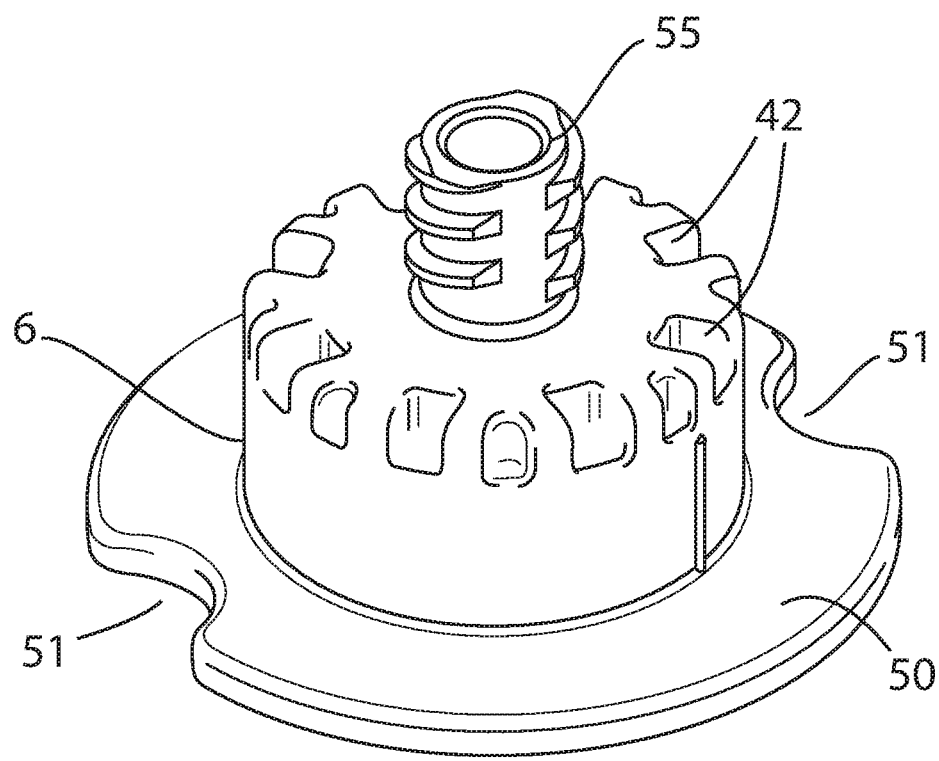
FIG. 9 is a perspective view of a hub part of the device.
Figure 10:
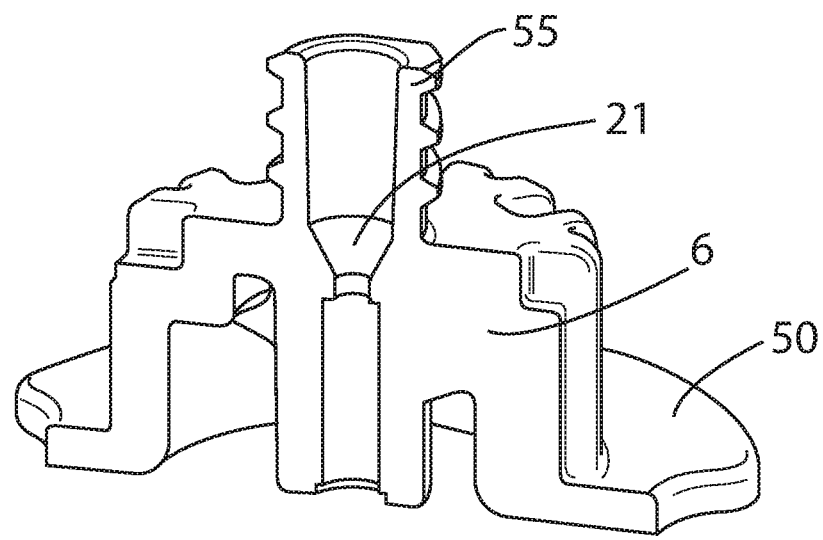
FIG. 10 is a cut-away view of the hub part.
Figures 11, 12, 13, 14, 15:
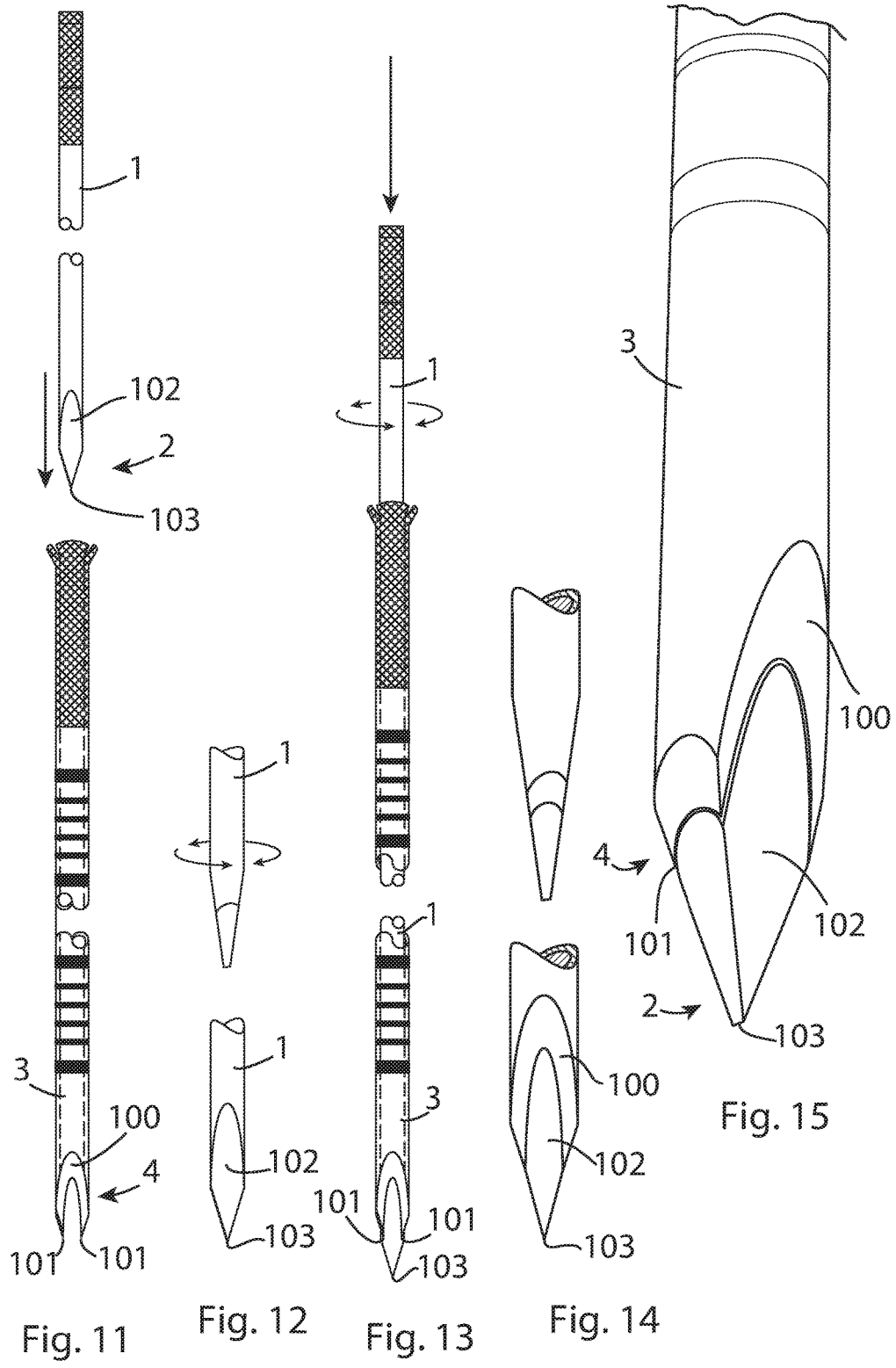
FIG. 11 is an exploded view illustrating the stylet being inserted into the cannula.
FIG. 12 are views of the stylet tip.
FIG. 13 is a view illustrating the stylet inserted into the cannula.
FIGS. 14 and 15 illustrate the engagement of the tip of the stylet and the tip of the cannula.

Referring to the drawings there is illustrated an intraosseous device according to the invention which comprises a stylet 1 with a pointed needle end 2 for penetrating tissue and bone and a cannula 3 through which the stylet 1 extends. The cannula 3 has a bone penetrating end 4. The upper end of the stylet 1 is mounted to a handle body 5 and the upper end of the cannula 3 is mounted to a hub 6 which is releasably mountable to the handle body 5. The device also includes a handle cover 7. A removable protective tube 8 may be provided for the stylet 1 and cannula 3 before use.

The stylet 1 has a bent portion 10 at the handle end and the handle body 5 has a receiver 11 for receiving and retaining the bent portion 10 of the stylet 1. The bent portion 10 has a roughened surface, which may be generated by grit blasting, for example, for enhanced engagement with an adhesive which further fixes the bent portion 10 in the handle body 5 in a manner than prevents rotation of the stylet 1 relative to the handle body 5 when manual torque is applied to penetrate tissue and bone, in use.

The bent portion 10 of the stylet extends at an angle of from 10° to 30°, about 20° to the longitudinal axis of the stylet. We have found that this angle optimally achieves optimum engagement in the handle without sacrificing the strength and torqueability of the stylet.

The cannula 3 has an outwardly extending flare 20 at the hub end. In this case the flare is a split flare which is engaged in a corresponding seat 21 in the hub 6. The flared hub end also has a roughened surface 22, which may be generated by grit blasting, for example, for enhanced engagement with an adhesive which further fixes the hub end of the cannula 3 in the hub 6 in a manner that prevents rotation of the cannula 3 relative to the hub 6 when manual torque is applied, in use.

The bend 10 at the handle end of the stylet 1 engages in the receiver of the handle. This ensures that the stylet 1 cannot rotate independently of the handle 5, regardless of the level of manual torque applied. The hub end of the cannula 3 is flared and this was found to be able to withstand up to 10 times more torque than a straight sand-blasted surface. The result of the reinforcement of the stylet 1 and the cannula 3 is an exceptionally strong and robust manual intraosseous device.

The cannula has a series of markings 25 that are used to indicate to a user the length that the cannula has penetrated into bone. These graduated markings allow for better localisation at hospital and monitoring of the penetration depth. Every 5 mm along the length of the cannula the circumferential markings are thicker to make it easier again for the user to quickly examine the depth of penetration. This is important to the user as if the cannula penetration depth has moved, it may indicate that the cannula has moved out of the bone.

The handle body 5 has a socket 30 to receive a corresponding spigot 31 of the handle cover 7. The handle cover 7 also has a ledge 35 extending around the periphery thereof and a depending wall 36 which engages with a corresponding recess 37 in the handle body 5. The handle body 5 is reinforced with various ribs 38. Similarly, the handle cover 7 also has reinforcing ribs 39.

The handle body 5 and the handle cover 7 are generally rectilinear in transverse cross section with rounded corners for ease of gripping by the user somewhat like the handle of a screwdriver for ease of gripping and application of torque by a user. The handle parts 5, 7 may have various additional external recesses and/or ribs to aid gripping.

The hub end of the handle body 5 has a recess 40 and a series of circumferentially spaced-apart formations 41 that engage with corresponding recesses 42 at a handle end of the hub 6. The interlocking engagement between the handle and hub formations/recesses 41, 42 are highly effective for torque transmission.

The hub 6 has a circumferential flange 50 which widens the region of contact between the device and the patient. The flange 50 has cut-away regions 51 to facilitate gripping engagement of a user's fingers with the hub 6. The hub 6 also has a luer connector 55 for engagement with a luer of another device such as an intraosseous extension set that connects to the fluids to be administered.

Referring to FIGS. 11 to 15, the stylet 1 and cannula 3 are shown in more detail. The end 4 of the cannula has two bevelled edges 100 which define two cutting tips 101. The bone retracting end of the stylet 1 also has bevelled edges 102 which define a single cutting tip 103. In the correct alignment of the stylet end and the cannula end, the cutting tip 103 of the stylet projects beyond the cutting tips 101 of the cannula and the bevelled edges 100 of the cannula and the bevelled edges 102 of the stylet are aligned and flush with each other for optimum penetration and cutting efficiency.

Figure 16:
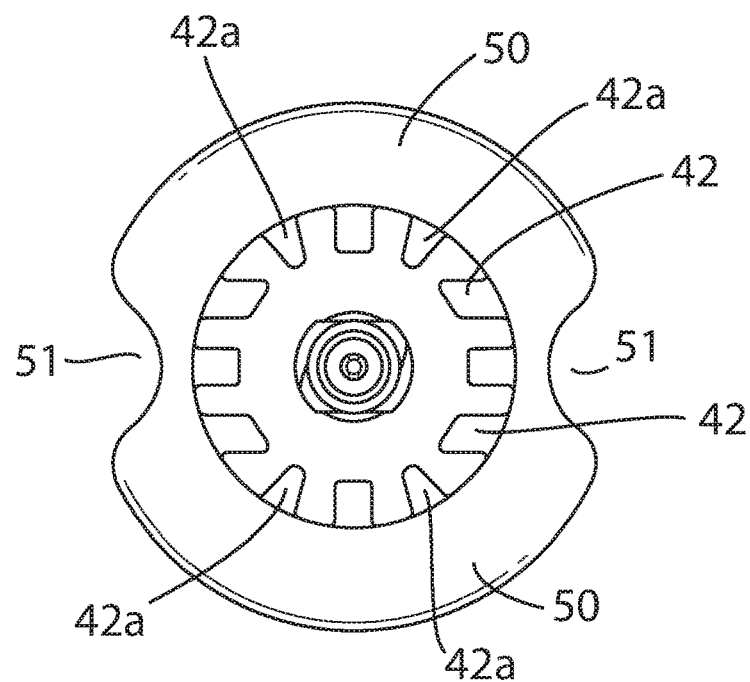
FIG. 16 is a top plan view of the hub showing hub engagement formations.
Figure 17:
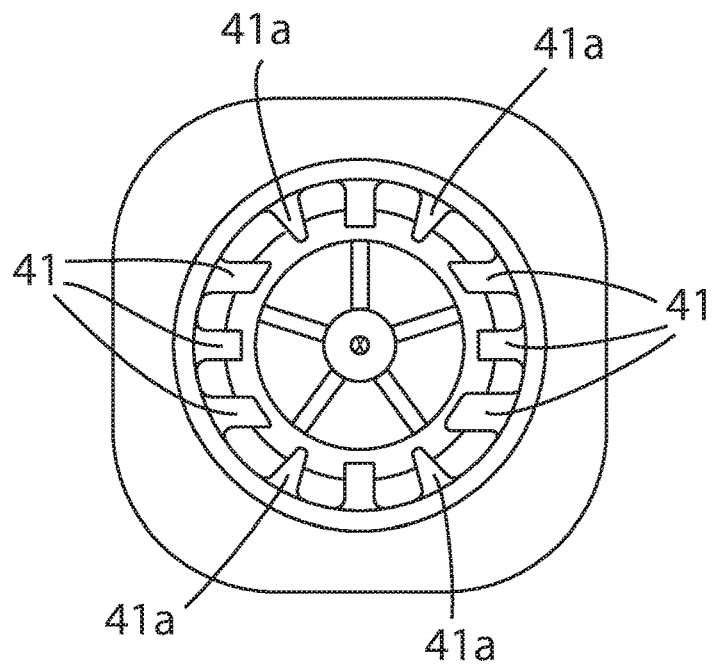
FIG. 17 is an underneath plan view of the handle showing handle engagement formations.
Figure 18:
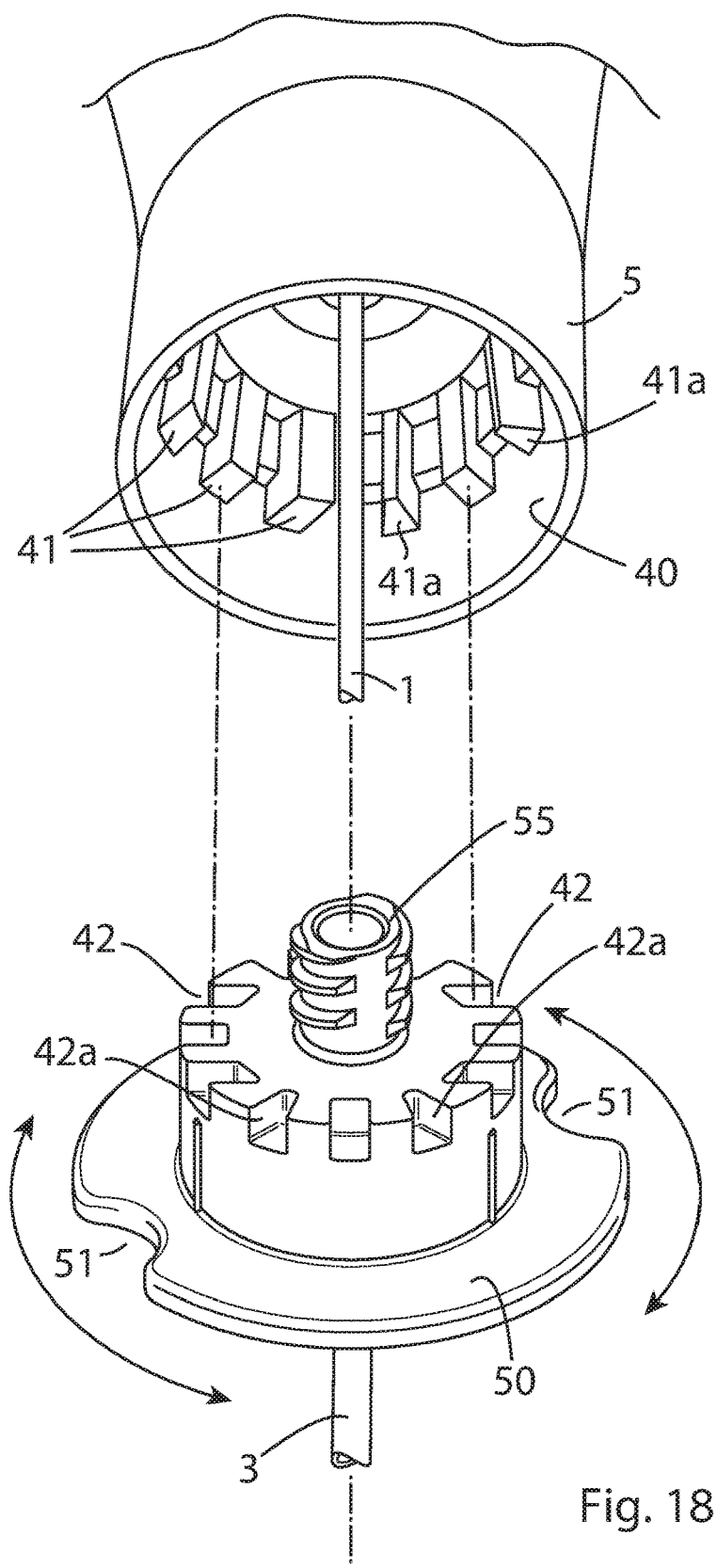
FIG. 18 is an exploded view illustrating the engagement of the hub formations with the handle formations.

The engagement of the handle 7 and hub 6 are shown in more detail in FIGS. 16 to 18. The hub end of the handle body 5 has a recess 40 for receiving the hub 6 and a series of circumferentially spaced-apart formations 41 that engage with corresponding hub formations 42 at a handle end of the hub 6. In use, the handle is rotated and the handle formations 41 engage with the hub formations 42. This results in an interlocking engagement of the handle 7 and hub 5 and allows for effective torque transmission which is particularly advantageous as the device is manually operated.

The handle formations 41 and the hub formations 42 only interlock when the tip of the stylet and the tip of the cannula are aligned for optimum bone penetration.

Importantly, the engagement between the hub and the handle allows for both clockwise and anticlockwise twisting. This is important to ensure that the stylet and the cannula are aligned for optimum bone penetration and also to facilitate the natural twist tendencies of both left and right handed users. The engagement system also provides for significant torque strength which is necessary to achieve manual penetration of bone.

The handle formations 41 and the hub formations 42 are engagable only in a set number of engagement configurations of the handle relative to the hub. In some cases the set number may be one. In the embodiment illustrated the set number is two and the engagement configuration are at 180° to each other.

In the aligned configuration, the handle 5 is movable downwardly for interlocking the handle formations 41 with the hub formations 42.

The plurality of hub formations 42 comprise formations of differing shapes and the plurality of handle formations 41 comprise formations of differing shapes. In the engaging configuration, handle formations 41 which are of the same shape as formations 42 of the hub are aligned.

In some cases the formations comprise ribs and corresponding recesses which may be of generally polygonal shape.

The formations in this case comprise at least one dovetail formation 41a of the handle which in the engaged configuration is engaged with a corresponding dovetail formation 42a of the hub. In one embodiment the handle comprises a pair of dovetail formations 41a which are diametrically opposed and the handle comprises two pairs of dovetail formations 41a of matching size and shape to the hub dovetail formations 42a. The formations are shaped for ease of effective interlocking engagement In use, when access is required to the bone marrow the protective tube 8 is removed which exposes the pointed end 103 of the stylet 1. The user grasps the device firmly and a torqueing action is used to force the stylet and the following cannula tip to penetrate bone. The handle part 5 and stylet 1 are then removed leaving the luer 55 on the hub 6 exposed for connection to an extension set that connects to fluids to be administered. Fluids are administered through the cannula 3.

Figure 19:
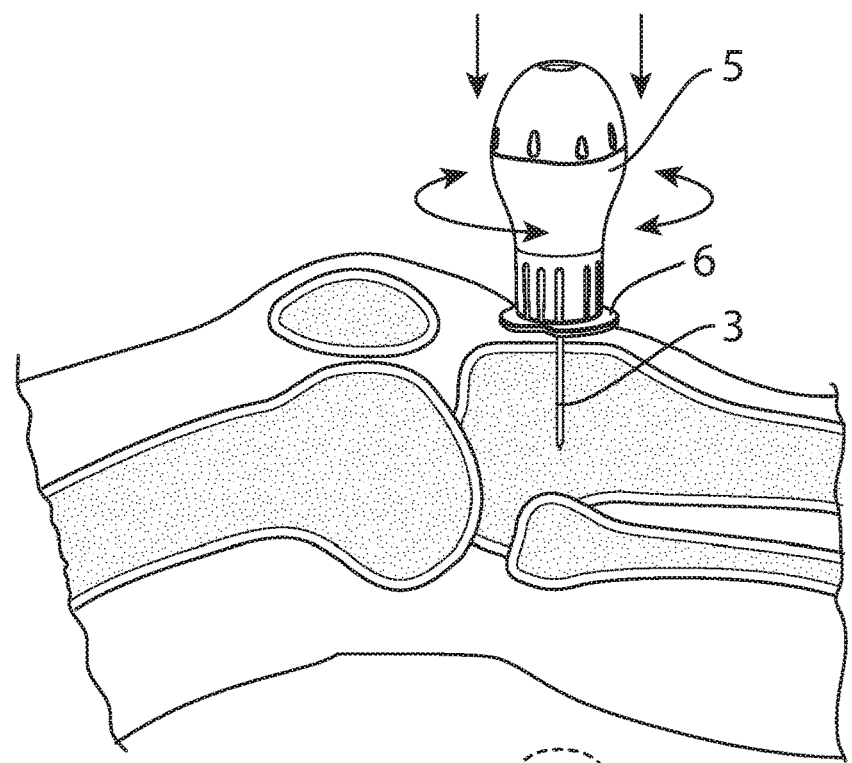
FIG. 19 is a diagram of the device being inserted into the bone of a patient.
Figure 20:
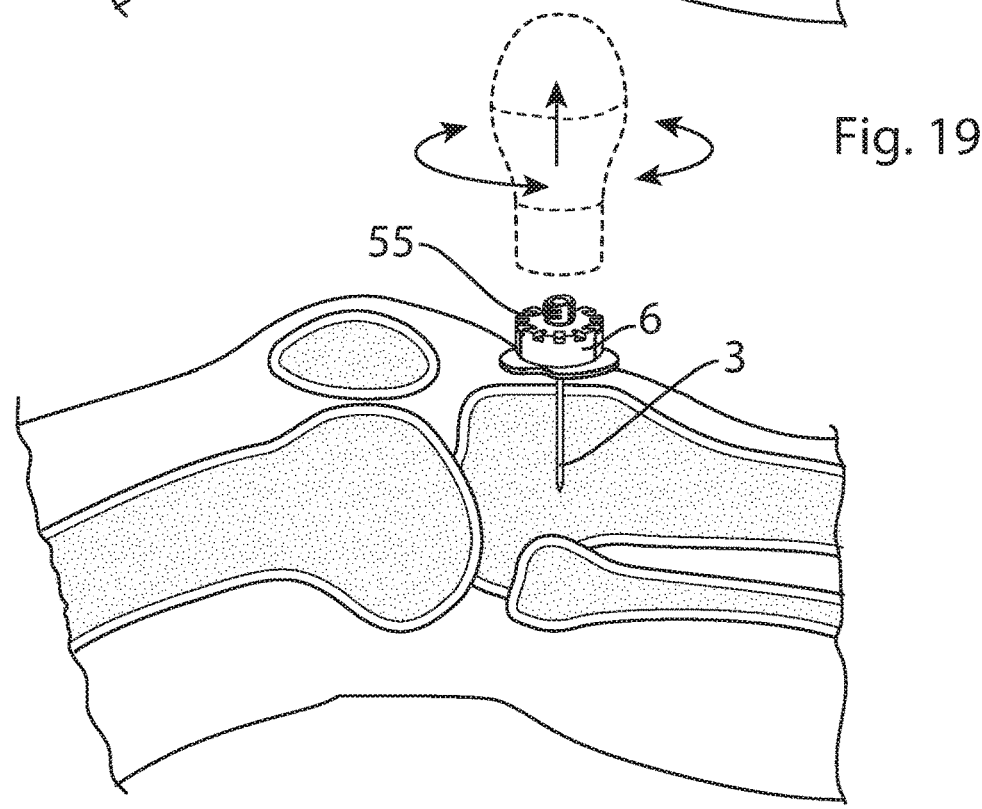
FIG. 20 is a view of the intraosseous device with the handle removed.

Referring to FIGS. 19 and 20, there is illustrated the intraosseous device of the invention inserted into a patient. The rotation in both an anti-clockwise and a clockwise direction are illustrated by arrows.

Figure 21A:
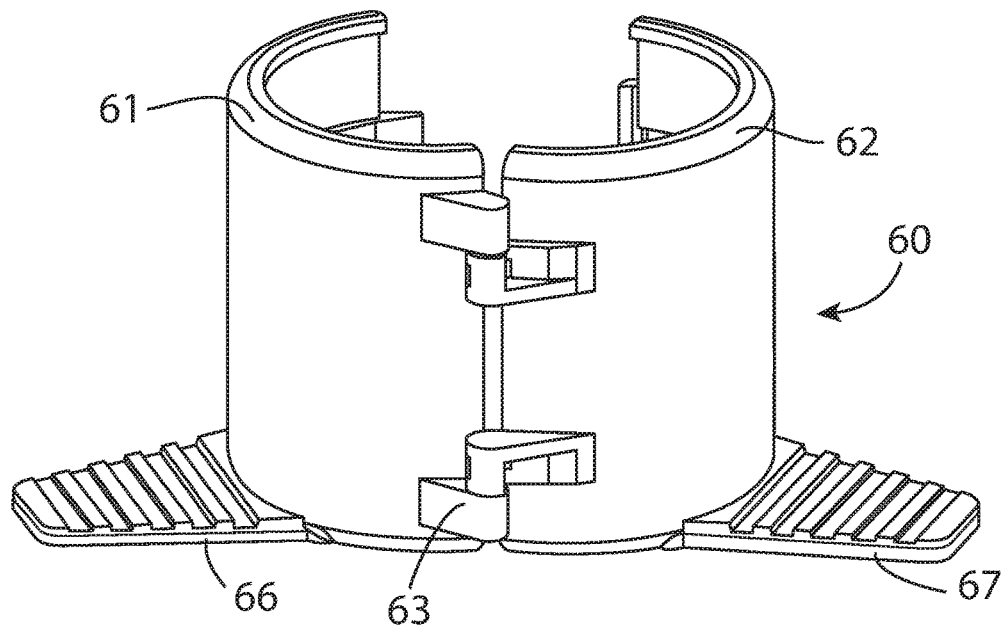
FIGS. 21(a) and 21(b) are perspective views of a stabilising anchor.
Figure 21B:
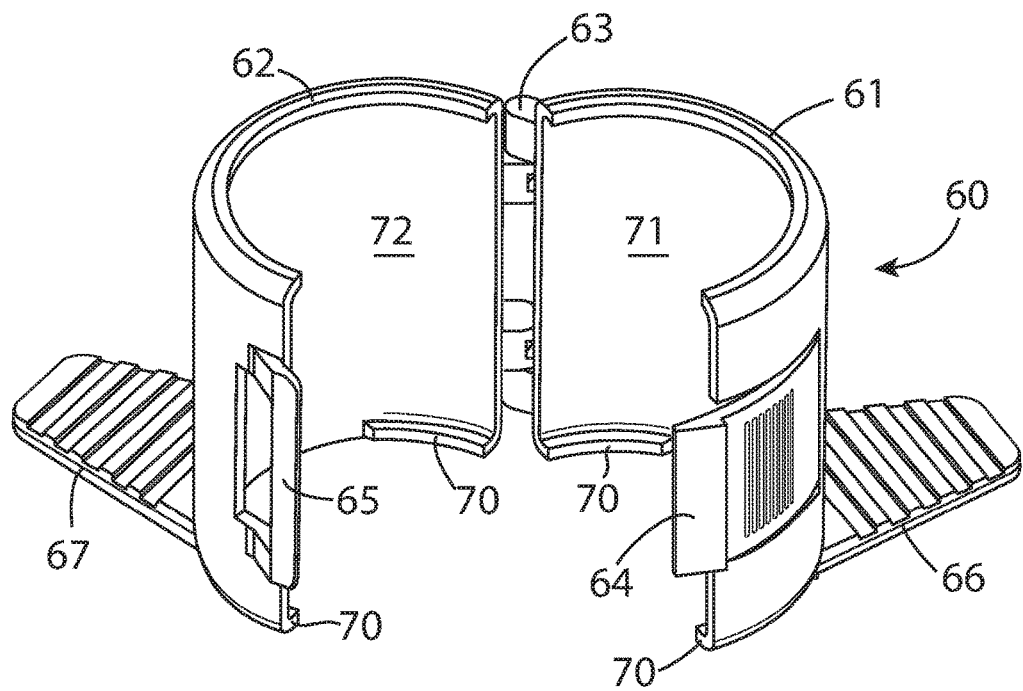
Figure 22:
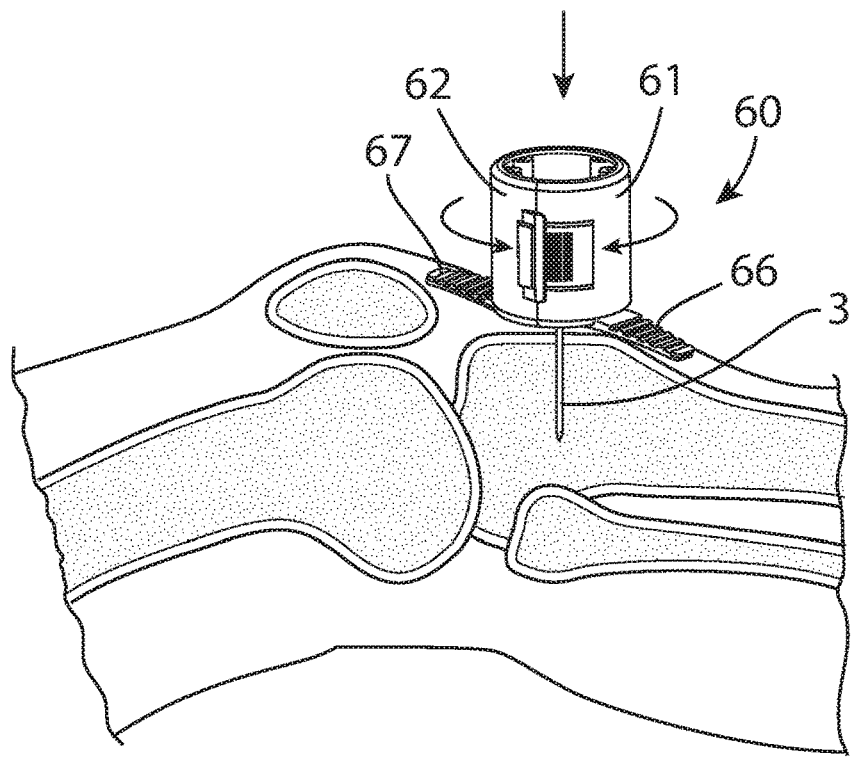
FIGS. 22 and 23 are perspective views of the stabilising anchor in use with the intraosseous device.
Figure 23:
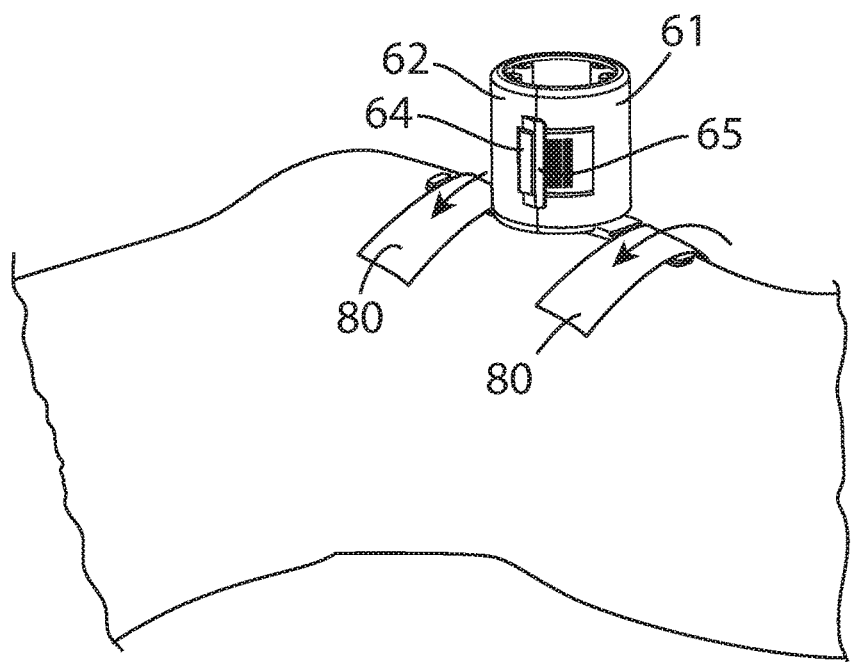

Referring to FIGS. 21 to 23 there is illustrated a stabilising anchor 60 which is used to anchor the intraosseous device 1 in use, for example to the patient. The stabiliser 60 comprises a pair of half cylindrical elements 61, 62 which are hinged together 63 on one side. A locking system comprising a locking strip 64 on one element 61 and a receiver 65 on the other element 62 is provided on the other side of the elements 61, 62. Side wings 66, 67 extend outwardly from the elements 61, 62 for mounting to a patient, for example by using an adhesive on the underside of the wings 66, 67 which is exposed when a cover is removed from the underside of the wings 66, 67. More commonly an adhesive tape 80 may be used over the wings for securing to the patients skin as illustrated in FIG. 23.

The stabiliser 60 has mounting features for engaging the stabiliser with the intraosseous device. The mounting features include an inturned ledge 70 which in use defines a receiver which engages with the outer periphery of the hub flange 50.

The inner surfaces 71, 72 of the elements 61, 62 are cushioned to adjust to the intraosseous device. Such cushioning may be constructed from foam or similar based polymers.

Many patients where intraosseous access is administered require quick transport. Such transport can result in dislodgement of the intraosseous device. The stabiliser helps to protect the device from dislodgement so that uninterrupted administration of fluids can occur. Additionally it is designed to fit and secure the cannula by gripping the hub at any height. This allows for multiple depth securements as the penetration depth may be different from patient to patient. It is also unlikely that the user will insert the cannula in such a way that the hub 50 is at exactly 90 degrees to the skin surface. The cushioning allows for stabilisation even if the cannula is not inserted at a 90 degree angle.

Additionally, the stabiliser can be closed on the hub one handed by the user. This is made possible by the combination of the hinge 63 and the locking mechanism 64, 65. Finally the ribbed wings 66, 67 are flexible, allowing for conforming to the patients skin surface at the cannula insertion site. Once secured with tape this allows for a robust stabilisation of the cannula.

The stabiliser can be fitted to the device hub and closed around it and locked. Once in place around the hub medical tape 80 can be placed over the wings to secure these to the patient's skin. This stabilises the device for continued fluid administration or transport. FIGS. 22 and 23 illustrate the use of the stabiliser of the invention in more detail. There is illustrated a stabilising anchor 60 which is used to anchor the intraosseous device 1 in use, for example to the patient. The stabiliser 60 comprises a pair of half cylindrical elements 61, 62, with side wings 66, 67 extend outwardly from the elements 61, 62 for mounting to a patient. In FIG. 23, it can be seen that adhesive strips 80 are used to secure side wings 66 and 67 to the patient.

The handle may be gripped by a user and/or may be driven by any suitable accessory or tool such as a powered driver. For example, the handle may be releasably engagable with a powered tool, either directly or by using a suitable adaptor that engage with the handle and the powered driver. For example, the handle may have formations such as those described above which are engagable with a powered driver. In this way the device can be manually operated and/or assisted by a power driver. In the case of the device of FIGS. 1 to 20, the lid part 7 of the handle may be removed and the powered tool engaged with the upper end of the handle formations.

Figure 24:
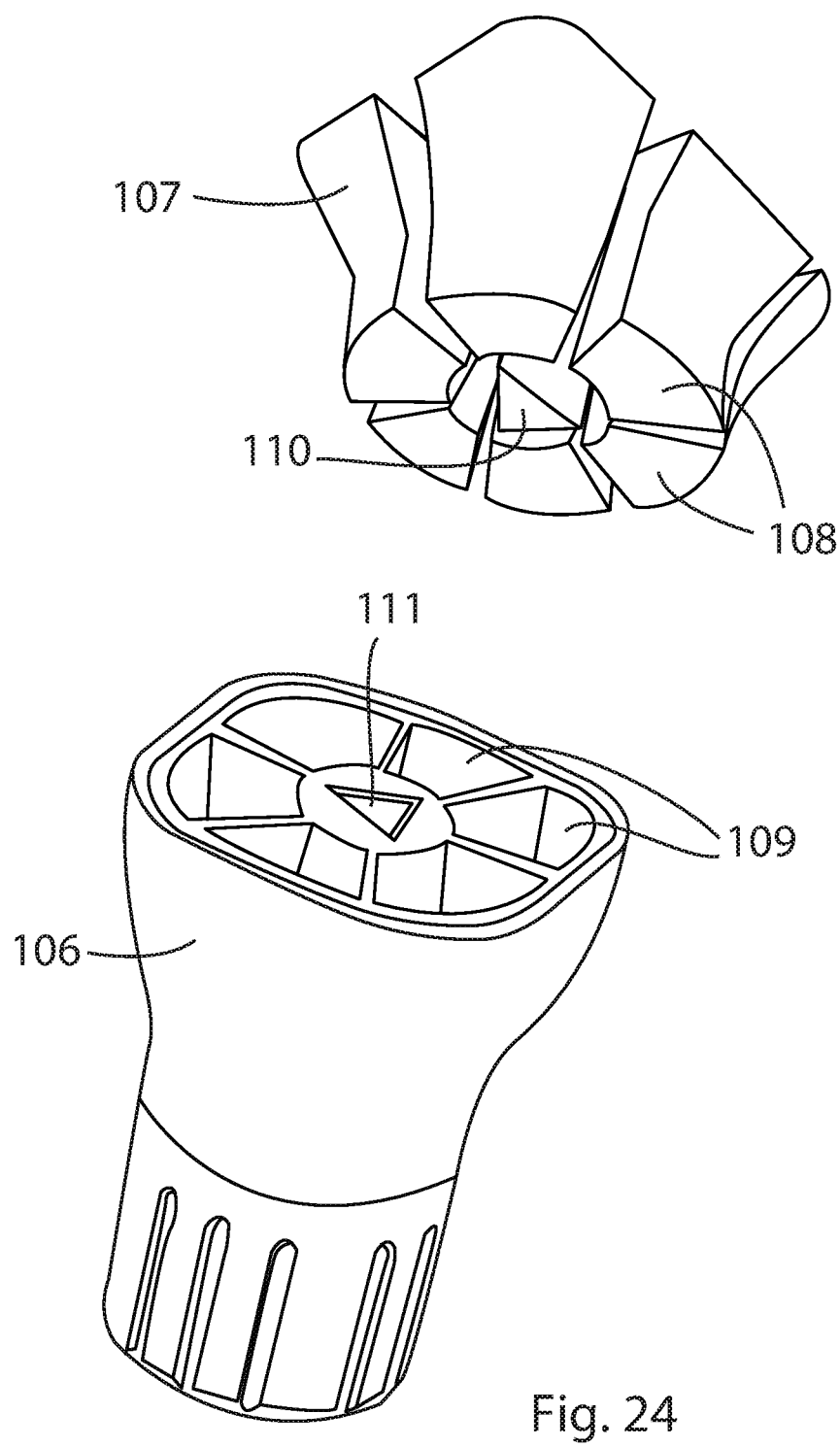
FIG. 24 is a perspective view of portion of another intraosseous device according to the invention.

Another example of such a device can be seen in FIG. 24. In this example, the device is illustrated in association with a powered driving tool. The device comprises a hub and a handle 106, which are releasably mounted with a stylet mounted to the handle and a cannula mounted to the hub, as in previous embodiments. In this case the handle 106 is illustrated being releasably engaging with a powered driver for torque transmission.

The handle 106 has formations adapted to receive portions of a powered driver end 107, so that the handle 106 and powered driver 107 inter-engage.

The powered driver end 107 has circumferentially spaced-apart formations 108 for engaging with corresponding recesses 109 of the handle 106. In addition, the driver 107 has a central formation 110 for engaging with a central recess 111 in the handle 106. This configuration of inter-engaging formations has the advantage of providing central, as well as radially spaced apart engagement, resulting in a secure connection and significant torque strength.

The handle 106 may have rounded corners and may have additional external recesses and/or ribs to aid gripping, so that in use the handle 106 can be held in place for the reception of the power driver formations 108, 110.

Upon engagement of the formations of the handle 106 and the formations of the driver connector 107, the power driver is releasably connected to the handle 106.

The power driver comprises a drive shaft, a motor for providing the rotary motion to the drive shaft, a power supply and electronic circuitry. The motor provides rotary motion to the drive shaft, which has one end, 107, for connecting with the handle 106. This rotary motion may be provided via a gear assembly, so that the frequency of rotation of the drive shaft can be increased or decreased.

It is envisaged that a set of switches may also be used to control the use of the power device. For example, there may be a switch for turning on and off the power of the device and another for increasing or decreasing the speed of rotation of the drive shaft. There may also be another switch for anti-clockwise and clockwise rotation of the drive shaft.

Upon activation of the power device the motor provides a rotary motion to the drive shaft, which rotates the handle of the device and transmits torque to the stylet and the cannula for bone penetration of the patient.

The device can be inserted into bone at any desired location including a humeral head, a proximal tibia, and a distal tibia. Typical procedures using the intraosseous device are as follows.

Insertion Steps
1. Prepare the intended insertion site with antiseptic solution.
2. Hold the handle 57 in the palm of the hand and place thumb and index fingers in the hub fingers slots.
3. Puncture the skin at the insertion site and push the needle 1 through subcutaneous tissue until bone contact.
4. Begin bone insertion with the needle 1 at a 90° angle at the surface using a steady twisting/rotation action along with gentle inward pressure.
5. As the needle tip 103 enters the bone, continue advancing the cannula and stylet with a steady clockwise and anticlockwise rotation/twisting through the cortex of the bone until a slight give is felt (i.e. loss of resistance). The device is designed to cut using this twisting/rotation and only gentle pressure against the bone is needed.
6. When loss of resistance is felt, the needle trocar stylet 1 is removed by stabilising the cannula hub 3 and withdrawing the handle 5 with the stylet mounted to it. The stylet is disposed of in sharps containment. No handle twisting is required to disengage. The handle 5 can be pulled upwardly for removal.
7. The provided connection extension set is primed with saline and connected to the Leur lock connection 55 on the cannula hub 6.
8. The position of the intramedullary needle is confirmed by aspirating a small visual quantity of bone marrow and then the cannula is flushed with an appropriate volume (e.g. 10 ml in adults) of 0.9% saline.
9. After flushing, medication/fluids can be administered.
10. The cannula hub 6 is stabilised by using the stabilisation device.
    a) The stabilisation device is opened by unclasping the locking mechanism (64, 65).
    b) The stabilisation device is placed around the cannula hub 6 with the wings (66, 67) based against the skin (for tibia, the stabilisation device is placed with the wings in line with the long axis of the bone).
    c) The stabilisation device is then closed until a click is heard as a result of engagement of the locking mechanism 64, 65. Tape 80 is then applied across wings 66, 67.

Removal of the Device

The stabilisation device, if it has been applied, is removed first. Then, the cannula hub in a clockwise and anticlockwise motion as the cannula is pulled straight out from the bone. If achieving grip on the needle cannula hub is difficult then a Leur syringe may be connected directly to the Leur lock connection 55 and gently twisted in a clockwise direction as the syringe/needle hub is pulled out. Once removed, the cannula 3 is placed in an appropriate sharps container.

It will be apparent from the foregoing description that, while particular embodiments of the present invention have been illustrated and described, various modifications can be made without departing from the spirit and scope of the invention. For example, while embodiments may refer to particular features, the invention includes embodiments having different combinations of features. The invention also includes embodiments that do not include all of the specific features described.

The invention is not limited to the embodiments hereinbefore described, which may be varied in construction and detail.

The invention claimed is:
1. An intraosseous device comprising:
   a handle;
   a hub which is releasably mounted to the handle;
   a stylet having a handle end mounted to the handle; and
   a cannula having a hub end mounted to the hub,
   the handle end of the stylet having a bent portion and the handle having a receiver for the bent portion of the stylet for non-rotatably fixing the stylet to the handle;
   the hub end of the cannula having an outwardly extending flare for non-rotatably fixing the cannula to the hub;
   the handle and the hub having interengagable formations for torque transmission to the stylet and the cannula for bone penetration in either clockwise or counter-clockwise rotation of the device,
   the formations including a plurality of circumferentially spaced-apart handle formations that are engagable with a plurality of corresponding formations of the hub,
   the plurality of hub formations include formations of differing shapes and the plurality of handle formations include formations of differing shapes and wherein, in the engaged configuration, handle formations of the same shape as hub formations are aligned,
   the handle being rotatable relative to the hub from a disengaged configuration in which the handle formations are not aligned with the hub formations to an aligned configuration in which the handle formations are aligned with the hub formations,
   wherein, in the aligned configuration, the handle is movable axially for interlocking the handle formations with the hub formations, and
   wherein, in the interlocked configuration, a tip of the stylet extends from a distal end of the cannula and a beveled edge of the stylet is aligned with a beveled edge of the cannula.
2. The intraosseous device as claimed in claim 1, wherein the handle formations and the hub formations are engagable only in a set number of engagement configurations of the handle relative to the hub.
3. The intraosseous device as claimed in claim 2, wherein the set number is one.
4. The intraosseous device as claimed in claim 2, wherein the set number is two and the engagement configurations are at 180° to each other.
5. The intraosseous device as claimed in claim 1, wherein the formations are of generally polygonal shape.
6. The intraosseous device as claimed in claim 1, wherein the formations include at least one dovetail formation of the handle which in the engaged configuration is engaged with a corresponding dovetail formation of the hub.
7. The intraosseous device as claimed in claim 6, wherein the handle includes a pair of dovetail formations which are diametrically opposed.
8. The intraosseous device as claimed in claim 7, wherein the handle includes two pairs of dovetail formations.
9. The intraosseous device as claimed in claim 1, wherein the hub comprises a luer connector which is exposed on removal of the handle.
10. The intraosseous device as claimed in claim 1, wherein the formations include ribs and corresponding recesses.

11. The intraosseous device as claimed in claim 1, wherein the bent portion of the stylet extends at an angle of from 10° to 30° to a longitudinal axis of a main body of the stylet.

12. The intraosseous device as claimed in claim 11, wherein the bent portion of the stylet extends at an angle of about 20° to the longitudinal axis of the stylet.

13. The intraosseous device as claimed in claim 1, wherein the bent portion of the stylet has a roughened surface.

14. The intraosseous device as claimed in claim 1, wherein the hub end of the cannula includes a split flare.

15. The intraosseous device as claimed in claim 1, wherein the hub end of the cannula has a roughened surface.

16. The intraosseous device as claimed in claim 1, wherein the hub includes a circumferential flange part.

17. The intraosseous device as claimed in claim 16, wherein the flange part has cut-away regions to facilitate finger engagement with the hub.

18. The intraosseous device as claimed in claim 1, wherein the handle is configured for connection to a powered driver for torque transmission.

19. The intraosseous device as claimed in claim 18, wherein the handle includes formations for interengagement with corresponding formations of the powered driver.

20. The intraosseous device as claimed in claim 19, wherein the handle formations include a plurality of circumferentially spaced-apart formations that engage with a plurality of corresponding formations of the powered driver.

21. The intraosseous device as claimed in claim 20, wherein the handle has a central formation for engaging with a corresponding central formation of the powered driver.

22. A system comprising an intraosseous device as claimed in claim 1 and a powered driver which is adapted for releasable connection to the handle.

23. An intraosseous system comprising an intraosseous device as claimed in claim 1, and a stabilizer for stabilising the device, in situ.

24. The intraosseous system as claimed in claim 23, wherein the stabilizer includes mounting features for engaging the stabilizer with the intraosseous device, the stabilizer including side wings for mounting to the skin of a patient, the stabilizer includes a pair of half cylindrical elements which are hinged together on one side and which have a locking system for interlocking parts on an opposite side, the side wings extending outwardly from each of the half cylindrical elements, and the stabilizer includes cushioning to engage with the hub at different locations and/or orientations of the hub.

* * * * *